(12) United States Patent
Li et al.

(10) Patent No.: US 6,517,666 B2
(45) Date of Patent: Feb. 11, 2003

(54) AUTOMATIC DECAPSULATION SYSTEM UTILIZING AN INTEGRATED SPACER/PROTECTION PLATE

(75) Inventors: Xia Li, Fremont, CA (US); Jose Hulog, San Jose, CA (US); Mohammad Massoodi, Los Altos, CA (US)

(73) Assignee: Advanced Micro Devices, Inc., Sunnyvale, CA (US)

(*) Notice: Subject to any disclaimer, the term of this patent is extended or adjusted under 35 U.S.C. 154(b) by 0 days.

(21) Appl. No.: 09/818,382

(22) Filed: Mar. 27, 2001

(65) Prior Publication Data

US 2002/0139768 A1 Oct. 3, 2002

(51) Int. Cl.$^7$ ................................ H01L 21/00
(52) U.S. Cl. ................................ 156/345.11
(58) Field of Search .......................... 156/345.11

(56) References Cited

U.S. PATENT DOCUMENTS

| | | | | |
|---|---|---|---|---|
| 4,826,556 A | * | 5/1989 | Kobayashi | 156/345 |
| 5,252,179 A | * | 10/1993 | Ellerson et al. | 156/655 |
| 5,443,675 A | * | 8/1995 | Wensink | 156/345 |
| 5,766,496 A | * | 6/1998 | Martin | 216/56 |
| 5,783,098 A | * | 7/1998 | Martin et al. | 216/56 |
| 5,792,305 A | * | 8/1998 | Winsemius et al. | 156/345 |
| 5,855,727 A | * | 1/1999 | Martin et al. | 156/345 |

\* cited by examiner

Primary Examiner—Gregory Mills
Assistant Examiner—Michelle Crowell
(74) Attorney, Agent, or Firm—Sawyer Law Group LLP

(57) ABSTRACT

An automatic decapsulation system for a device is disclosed. The system comprises an etch plate, an etch head, a sheet coupled to the etch head, a rubber gasket disposed between the etch head and the sheet, and an integrated spacer and protection plate for securing the device without damaging the backside of the device during decapsulation. In one embodiment of the present invention, the integrated spacer and protection plate is adjustable to accommodate devices of varying sizes.

17 Claims, 6 Drawing Sheets

AUTOMATIC DECAPSULATION SYSTEM UTILIZING AN INTEGRATED SPACER/PROTECTION PLATE

CROSS-REFERENCE TO RELATED APPLICATIONS

The present invention is related to the following co-pending U.S. Applications: Automatic Decapsulation System Utilizing An Acid Resistant, High Heat Endurance and Flexible Sheet and a Method of Use, Ser. No. 09/551,300, filed on Apr. 18, 2000, and assigned to the assignee of the present invention; and Automatic Decapsulation System Utilizing An Acid Resistant, High Heat Endurance and Flexible Sheet Coupled to a Rubber Gasket and a Method of Use, Ser. No. 09/680,558 now U.S. Pat. No. 6,409 878 filed on Oct. 5, 2000, and assigned to the assignee of the present invention.

FIELD OF THE INVENTION

The present invention relates generally to automatic decapsulators and more particularly to the device protection unit utilized in such decapsulators.

BACKGROUND OF THE INVENTION

Automatic decapsulators are used to expose the die in any plastic package or device by etching away the die's plastic covering. Either fuming sulfuric, fuming nitric, or mixed fuming nitric and sulfuric acids may be used as an etchant. Decapsulation is a fast and safe process that produces a clean, uncorroded die surface. When fuming nitric acid is used as the etchant, there is little or no damage to the die surface or bond pads. Fuming sulfuric acid is normally used at an elevated temperature to remove the plastics that are not compatible with fuming nitric acid. The etching process is performed under pressure in an inert atmosphere to reduce metal oxidation and to reduce the production of harmful fumes.

FIG. 1a illustrates a side view of a typical system for automatic decapsulation of a device. The system 10 includes a safety cover 11 which is coupled to an etch plate 13. The system 10 also includes a positioning fixture 12 coupled to the etch plate 13 which is typically metal and is aligned with a package 16 and a gasket 14, typically made of rubber. The gasket 14 is positioned under the device 16 with an etch window in the gasket's center. During decapsulation, the device holder 20 presses down on the device 16, which presses down upon the rubber gasket 14, creating a tight seal with the etch head 18. The etchant is then provided by the etch head 18 through the etch window to the device 16.

For many current plastic packages, such as plastic ball grid array (PBGA) or fine ball grid array (FBGA) packages, solder balls are disposed on the backside of the package, i.e., on the face opposite to that exposed to the etchant. Decapsulating such packages is a challenge because the decapsulation temperature exceeds the melting point of the solder balls, and the solder balls can be deformed by the device holder. Moreover, some packages, like FBGA packages, can be as small as 5 mm on each side, thereby presenting alignment problems.

Co-pending U.S. patent application Ser. No. 09/680,558 entitled, "Automatic Decapsulation System Utilizing An Acid Resistant, High Heat Endurance and Flexible Sheet Coupled to a Rubber Gasket and Method of Use," filed on Oct. 5, 2000, and assigned to the assignee of the present invention, addresses some of the challenges faced when decapsulating ball grid array packages. According to one embodiment of the co-pending patent application, a spacer and a protection plate are disposed between the device and the device holder so that the device holder does not come in direct contact with the backside of the device. The spacer makes contact with the backside of the device only in areas without solder balls. Accordingly, the spacer prevents the protection plate from deforming the solder balls during decapsulation.

FIG. 2a illustrates a side view of the automatic decapsulation system 100 in accordance with the above-referenced co-pending application. The system 100 is similar to the system 10 of FIG. 1, and includes a safety cover 11' which is coupled to an etch plate 13'. As is seen, a spacer 108 is inserted between the backside of the package 110 and the protection plate 106. A rubber gasket 104 is placed between a gasket plate 102 and a head etch 18'. The spacer 108 is preferably made of a TEFLON sheet having a thickness of at least the height of the solder balls. TEFLON® is well known in the art. The generic term for TEFLON is polytetrafluoroethylene (PTFE). FIG. 2b illustrates a top view of the backside of the device 110 with the spacer 108 in accordance with the present embodiment. As is shown, a window is cut out of a sheet (not shown) to form the spacer 108, which surrounds and protects the solder balls. Accordingly, when the protection plate 106 is placed on top of the spacer 108, the plate 106 does not come in contact with the backside of the device 110, and the solder balls are protected from being crushed.

Although the above-described system in the co-pending patent application functions for its intended purpose, one of ordinary skill in the art will readily recognize that it would be desirable to improve the way in which the backside of the device is protected. For instance, it would be desirable to simplify the placement of the spacer, such that alignment with a very small device, such as a FBGA package, is accomplished with relative ease. It also would be desirable to devise a system in which the protection plate is easily put in place and kept in place during decapsulation. In addition, it would be desirable to reduce the cost and labor associated with manufacturing different spacers having different sizes to match the various package sizes.

Accordingly, what is needed is a system and method to overcome the above-identified problems. The system and method should be cost effective and easy to implement with existing processes and equipment. The present invention addresses such a need.

SUMMARY OF THE INVENTION

An automatic decapsulation system for a device is disclosed. The system comprises an etch plate, an etch head, a sheet coupled to the etch head, a rubber gasket disposed between the etch head and the sheet, and an integrated spacer and protection plate for securing the device without damaging the backside of the device during decapsulation. In one embodiment of the present invention, the integrated spacer and protection plate is adjustable to accommodate devices of varying sizes.

The integrated spacer and protection plate of the present invention automatically aligns the spacer with the device, thereby reducing the amount of time taken to otherwise align the spacer. In addition, because the spacer and protection plate are integrated, the protection plate is put in place and kept in place automatically. In a preferred embodiment, the integrated spacer and protection plate is manufactured from a TEFLON sheet, thereby providing a highly durable and cost efficient solution.

DETAILED DESCRIPTION

The present invention relates generally to automatic decapsulators and more particularly to the device protection unit utilized in such decapsulators. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

The present invention utilizes an integrated spacer and protection plate. The integrated spacer and protection plate is designed to be placed over the gasket for easy alignment. The integrated spacer and protection plate sits on the edge of the device and includes an area located over the device, which serves to protect any elements that may be situated on the backside of the device. During decapsulation, the device holder clamps down on the integrated spacer and protection plate, which in turn secures the device to the etch head.

The present invention will be described in accordance with two preferred embodiments. The present invention, however, is not limited to the described embodiments, and one skilled in the art would appreciate that different embodiments could exist which incorporate an integrated spacer and protection plate. Those embodiments would certainly fall within the spirit and scope of the present invention.

First Preferred Embodiment

Figure 1:
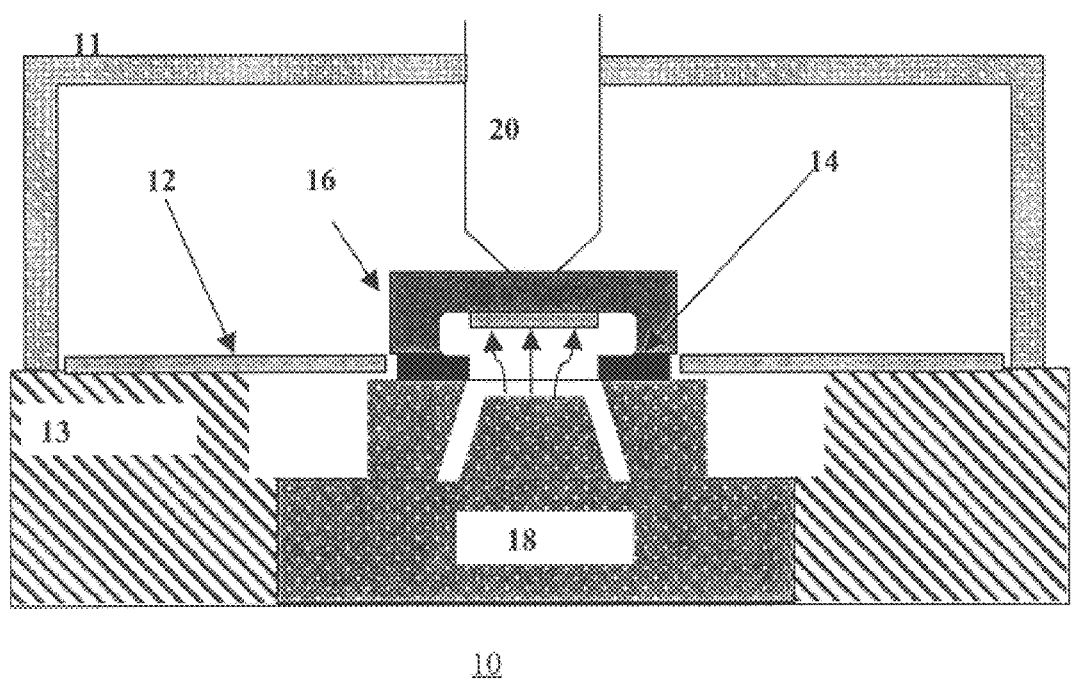
FIG. 1 illustrates a side view of a conventional system for autodecapsulation.
Figure 2A:
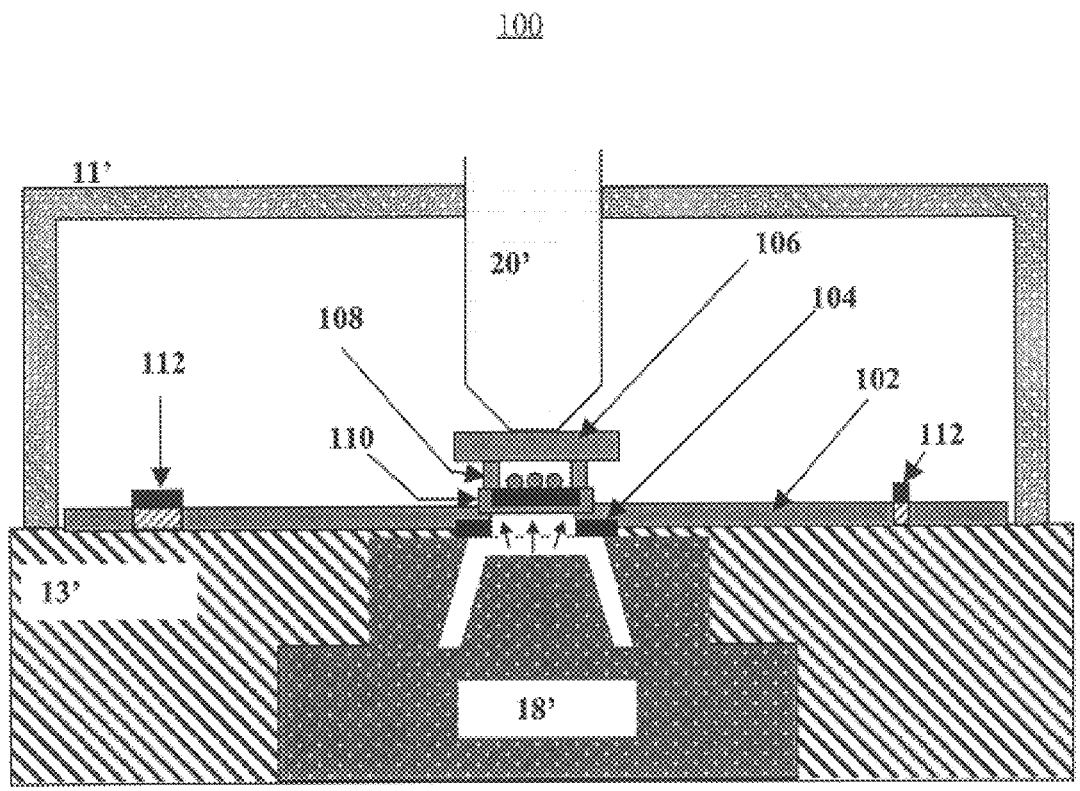
FIG. 2a illustrates a side view of the decapsulation system in accordance with the co-pending application.
Figure 2B:
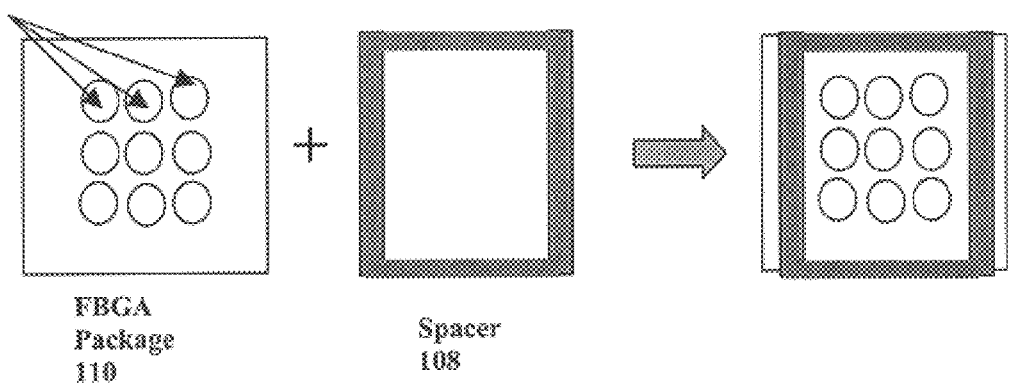
FIG. 2b illustrates a top view of the backside of the device and spacer in accordance with the co-pending application.
Figure 3:
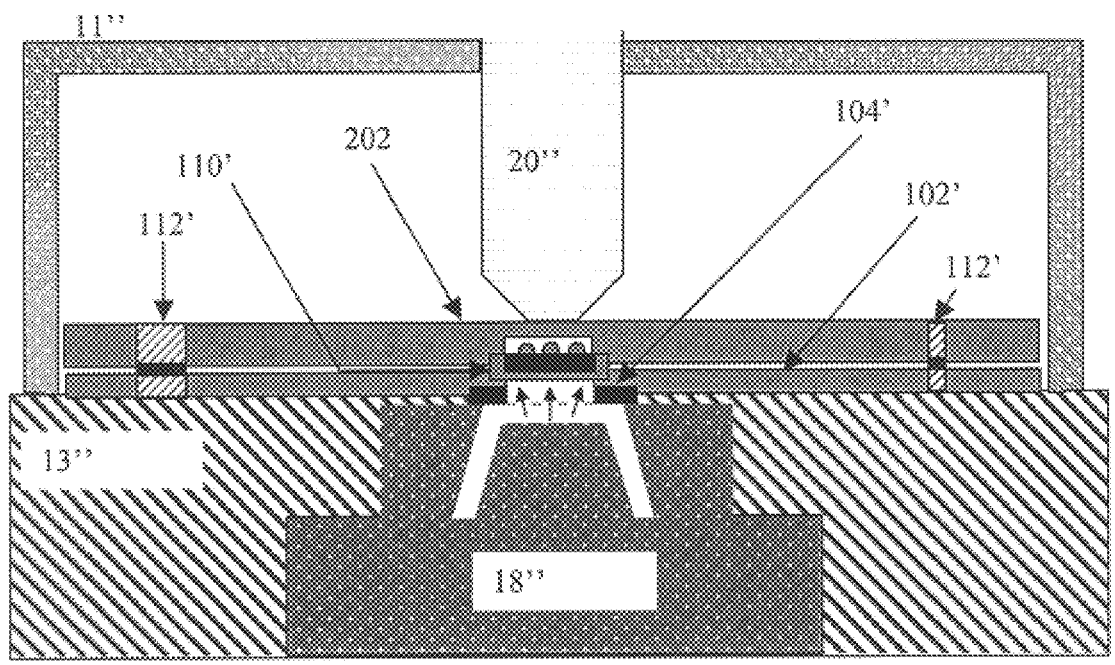
FIG. 3 is a side view of the decapsulation system in accordance with the first preferred embodiment of the present invention.

FIG. 3 illustrates a side view of the decapsulation system 200 in accordance with the first preferred embodiment of the present invention. The integrated spacer and protection plate 202 replaces the spacer 108 and protection plate 106 (FIG. 2a) utilized in the decapsulation system 100. A rubber gasket 104' is placed between a gasket plate 102' and a head etch 18". To simplify alignment, the integrated spacer and protection plate 202 is preferably similar in size to the gasket plate 102'. In one preferred embodiment, alignment is ensured by lining up holes 112' in the integrated spacer and protection plate 202 and the gasket plate 102' such that fixture pins (not shown) can be inserted through the holes 112' into the etch plate 13".

As is shown, the integrated spacer and protection plate 202 fits onto the package 110' and forms a cap over the solder balls. During decapsulation, the device holder 20" applies pressure down onto the integrated spacer and protection plate 202, which in turn presses the package 110' into the gasket 102', thereby creating a seal between the package 110' and the head 18".

Figure 4A:
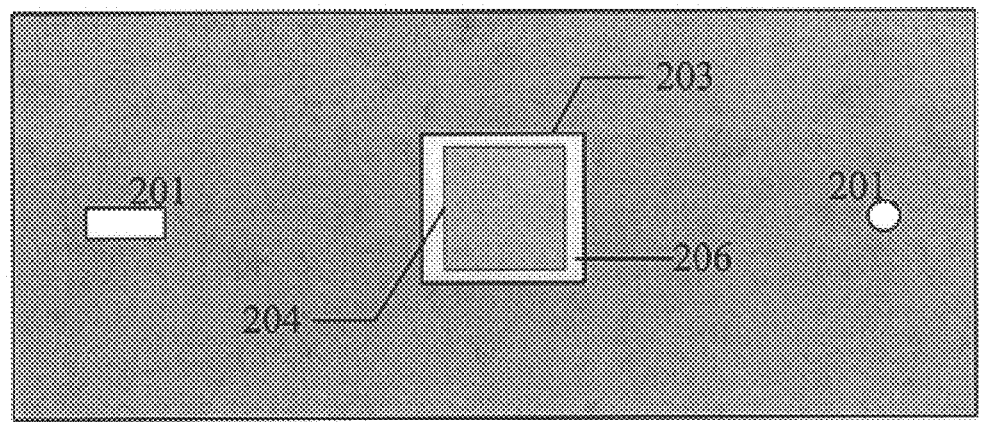
FIG. 4a illustrates a top view of the integrated spacer and protection plate in accordance with the first preferred embodiment of the present invention.
Figure 4B:
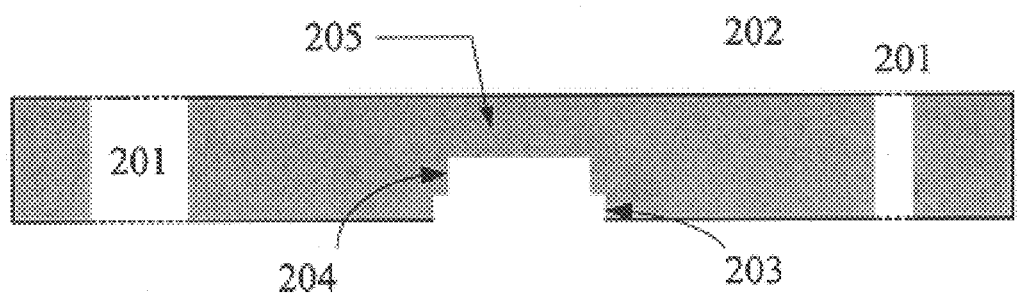
FIG. 4b illustrates a side view of the integrated spacer and protection plate in accordance with the first preferred embodiment of the present invention.

FIGS. 4a and 4b illustrate the top and side views, respectively, of the integrated spacer and protection plate 202 in accordance with the first embodiment of the present invention. As is shown in FIG. 4b, a multi-tiered trench is machined into the bottom surface of the plate 202. The first tier 203 is for holding the package 110' (FIG. 3) in place. The shape and size of the first tier 203 is substantially the same shape and size of the package 110'. The first tier's 203 height is preferably less than the package 110' standoff height when the package 110' is sitting on the TEFLON/Rubber gasket plate 102' (FIG. 3). As such, the plate 202 sits on the edge of the package 110', as opposed to sitting on the gasket plate 102'.

Referring back to FIGS. 4a and 4b, a second tier 204 is formed above the first tier 203. The second tier 204 is similar in shape, but smaller in size to the first tier 203. Preferably, the second tier 204 is 0.5 mm smaller on each side than the first tier 203. A rim 206 created between the first 203 and second 204 tiers acts as a spacer, making direct contact around the package 110' edges where no solder balls exist. The second tier 204 forms a cap 205 over the solder balls (not shown) and prevents them from being deformed during decapsulation. The height of the second tier 204 is preferably at least twice the height of the solder balls. So, for example, for small packages (FBGA), the height of the solder balls can range from 0.15 mm to 0.30 mm, and therefore, the height of the second tier 204 should preferably be at least 0.60 mm.

The integrated spacer and protection plate 202 according to the first embodiment of the present invention is preferably made from TEFLON or stainless steel. As mentioned above, the cap 205 is utilized as a protection plate, where the device holder 20" will apply pressure in order to seal the package 110' to the etch head 18" for decapsulation. Because TEFLON becomes somewhat pliable at decapsulation temperatures, the thickness must be sufficient to enable the cap 205 to withstand the pressure exerted by the device holder 20" without deforming. Accordingly, the thickness of the integrated spacer and protection plate 202 made from TEFLON is at least approximately 0.125 inches.

As is seen in FIG. 3, the package 110' sits in the gasket plate 102' and the integrated spacer and protection plate 202 fits directly over the package 110', such that the package 110' fits within the first tier 203 and contacts the rim 206. Because the spacer and protection plate are integrated, these elements are automatically aligned over the package 110' when the integrated spacer and protection plate 202 is set in place. Accordingly, what was once a tedious and time consuming task of placing a spacer and protection plate on top of a tiny device, now becomes a simple task that can be performed with relative ease.

Second Preferred Embodiment

A second preferred embodiment of the present invention is directed to an integrated spacer and protection plate, which is adaptable to packages having different sizes.

Accordingly, the second preferred embodiment of the present could be used for a variety of devices without the need for customization.

Figure 5:
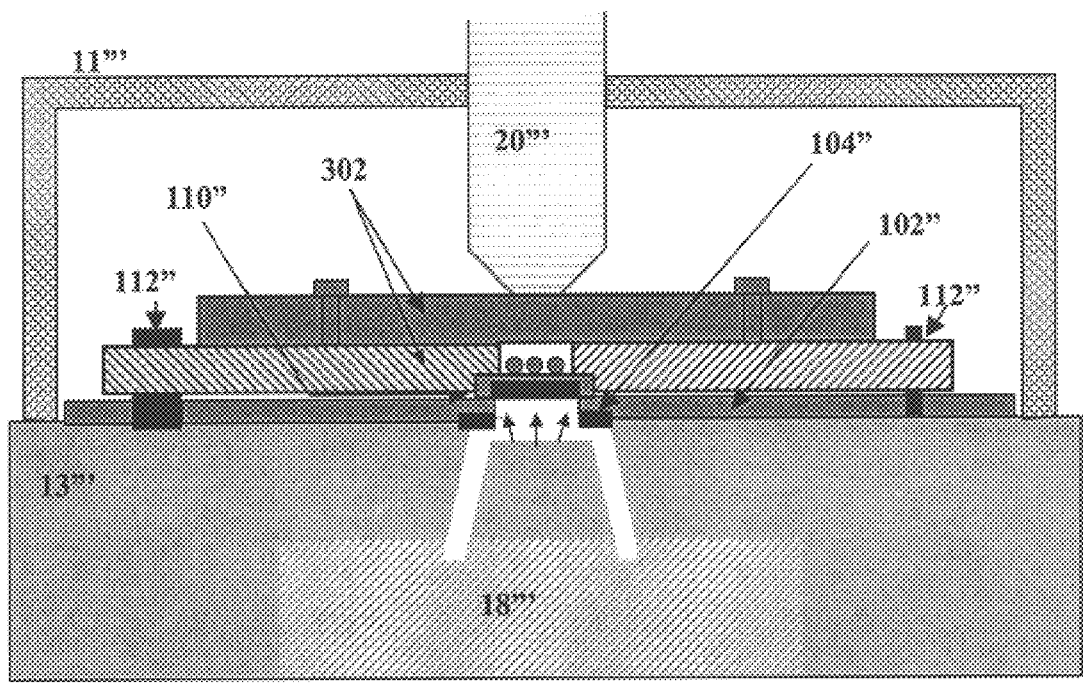
FIG. 5 is a side view of the decapsulation system in accordance with the second preferred embodiment of the present invention.

FIG. 5 illustrates a cross sectional view of the side of the decapsulation system 300 in accordance with the second preferred embodiment of the present invention. Like the first preferred embodiment, the integrated spacer and protection plate 302 replaces the spacer 108 and protection plate 106 (FIG. 2a) utilized in the decapsulation system 100. A rubber gasket 104" is placed between a gasket plate 102" and a head etch 18'''. To simplify alignment, fixture pins 112" extend through the gasket plate 102" and the integrated spacer and protection plate 302.

As is shown, the integrated spacer and protection plate 302 fits onto the package 110" and forms a cap over the solder balls. During decapsulation, the device holder 20''' applies pressure down onto the integrated spacer and protection plate 302, which in turn presses the package 110" into the gasket plate 102", thereby creating a seal between the package 110" and the etch head 18'''.

Figure 6A:
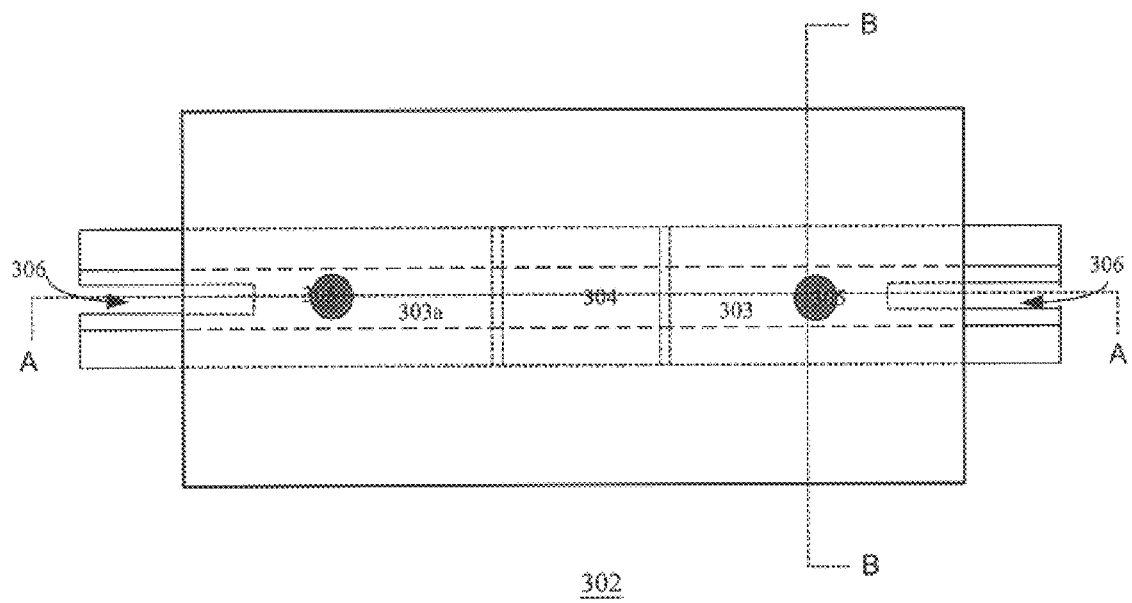
FIG. 6a illustrates a top view of the integrated spacer and protection plate in accordance with the second preferred embodiment of the present invention.
Figure 6B:
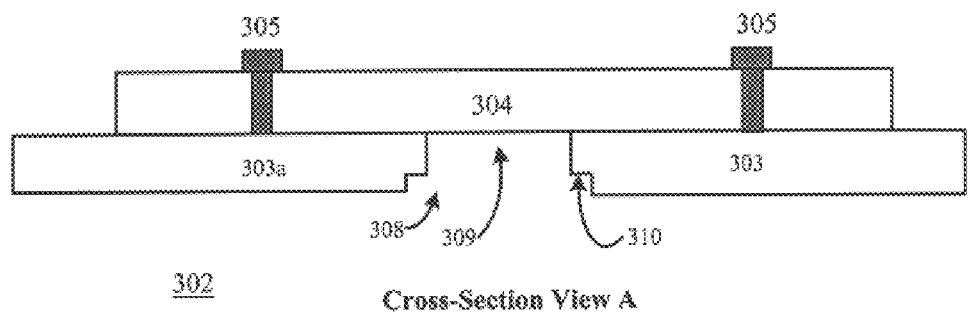
FIGS. 6b and 6c illustrate cross sectional views of the integrated spacer and protection plate in accordance with the second preferred embodiment of the present invention.
Figure 6C:
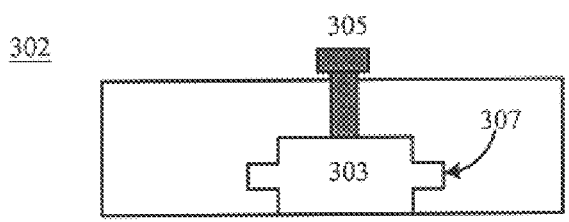

FIGS. 6a, 6b and 6c illustrate top and cross sectional views of the integrated spacer and protection plate 302 in accordance with the second preferred embodiment of the present invention. As is shown in FIG. 6b, the integrated spacer and protection plate 302 is a plate 304 that includes a plurality of bars (303, 303a) therein. The bars (303, 303a . . . ) slide horizontally along the length of the plate 304. As is seen in FIGS. 6a and 6b, a step 310 is formed on each bar (303, 303a) at an end facing the middle line of the plate 304. In FIG. 6a, a slot 306 is provided in each bar (303a, 303 into which the fixture pins 112" (FIG. 5) can be inserted for alignment purposes.

As is seen in FIG. 6c, each bar (303) slides along a notched slot formed within the plate 304. FIG. 6b shows that, in one embodiment, a first and a second bar (303, 303a) share the notched slot. When the first and second bars (303, 303a) are moved toward or away from the middle line of the plate 304, the opening created between the bars (303, 303a) contracts or expands.

Because the step 310 is provided on the bars (303, 303a), a first 308 and a second 309 opening is formed by the bars (303, 303a), as is seen in FIG. 6b. The first and second bars (303, 303a) are adjusted by sliding them toward or away from one another so that the first opening 308 is substantially the same size as a side of the package 110". The first opening 308 holds the package 110" in place. The height of the first opening 308 is preferably less than the package 110" standoff height when the package 110" is sitting on the TEFLON/Rubber gasket plate 102" (FIG. 5). Referring back to FIG. 6b, the step 310 created between the first 308 and second 309 openings acts as a spacer, making direct contact with the package 110" edge where no solder balls exist. The width of the step 310 is preferably 0.5 mm. The height of the second opening 309 is preferably at least twice the height of the solder balls.

Once the first 308 opening is adjusted to fit the package 110", the bars (303a, 303) are set in place by a plurality of pins 305 screwed down from the top of the plate 304. Referring back to FIG. 5, when the integrated spacer and protection plate 302 is put in place, the package 110" fits into the first opening 308 of the integrated spacer and protection plate 302 and the package 110" makes contact via the step 310. The solder balls are protected within the second opening 309, while the device holder 20''' applies pressure to the integrated spacer and protection plate 302 to secure and seal the package 110".

For today's FBGAs, the package size is far from standardized. In fact, packages can come in 30–40 different sizes. By being able to adjust the size of the first 308 opening, the integrated spacer and protection plate 302 can be used for a variety of packages having different sizes. This embodiment of the present invention also incorporates the positive attributes of the first preferred embodiment of the present invention, that is, easy alignment, cost effectiveness, and durability.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. An automatic decapsulation system for a device having a front side and a backside, wherein the front side is decapsulated, the system comprising:

an etch plate;

an etch head for providing an etchant;

a sheet coupled to the etch plate via a rubber gasket, the sheet for providing a gasket plate for the device and a seal between the device and the etch head; and a plate containing a plurality of movable bars for securing the device without damaging the backside of the device; wherein the plurality of bars slide toward and away from one another in a longitudinal direction along a notched slot in the plate; and wherein a step is provided on an end of each bar, the stepped end being closest to a middle line of the plate, such that the stepped end of each bar face each other.

2. The system of claim 1, wherein the plate has a top surface and a bottom surface, the bottom surface having a trench with at least two tiers, a first tier being substantially the same size as the device such that the device fits within the first tier.

3. The system of claim 2, wherein a second tier of the trench is smaller in size than the first tier, such that a rim is formed between the first tier and the second tier.

4. The system of claim 3, wherein the plate has a thickness and the at least two tiers has an overall height that is less than the thickness of the integrated spacer and protection plate.

5. The system of claim 4, wherein the plate is positioned over the device, the device fitting within the trench formed by the first tier, and the rim formed between the first tier and the second tier resting on the backside of the device; and wherein, the second tier forms a space above the backside, such that the device is protected from damage during decapsulation.

6. The system of claim 5, wherein the device is a ball grid array package having a plurality of solder balls on the backside.

7. The system of claim 6, wherein the rim rests on an area of the device not containing the plurality of solder balls, and wherein, the second tier has a height exceeding a diameter of a solder ball, such that the plurality of solder balls is protected during decapsulation.

8. The system of claim 7, wherein the rim is approximately 0.5 mm wide.

9. The system of claim 7, wherein the height of the second tier ranges from approximately 0.30 mm to 0.60 mm.

10. The system of claim 1, wherein the plurality of bars are adjusted to form a first opening having substantially the same size as a side of the device, the first opening being located on a bottom surface of the plate facing the device; and wherein a second opening is formed above the first opening, the second opening being smaller than the first opening by a width equal to twice a width of the step.

11. The system of claim 10, wherein the plate has a thickness and the first and second openings has an overall height less than the thickness of the plate.

12. The system of claim 11, wherein the device is a ball grid array package having a plurality of solder balls on the backside.

13. The system of claim 12, wherein the step rests on an area of the device not containing the plurality of solder balls, and wherein, the second opening has a height exceeding a diameter of a solder ball, such that the plurality of solder balls is protected during decapsulation.

14. The system of claim 13, wherein the step is approximately 0.5 mm wide.

15. The system of claim 13, wherein the height of the second opening ranges from approximately 0.30 mm to 0.60 mm.

16. The system of claim 1, wherein the plate comprises a polytetrafluoroethylene sheet, the polytetrafluoroethylene sheet having an approximate thickness of 0.125 inches.

17. The system of claim 1, wherein the plate further comprising a plurality of pins for keeping the plurality of bars in place.

* * * * *